(12) United States Patent
Lee et al.

(10) Patent No.: US 7,713,746 B2
(45) Date of Patent: May 11, 2010

(54) DIPSTICK ASSAY

(75) Inventors: Helen Lee, Cambridge (GB); Magda Anastassova Dineva, Cambridge (GB)

(73) Assignee: Diagnostics for the Real World, Ltd., Sunnyvale, CA (US)

( * ) Notice: Subject to any disclaimer, the term of this patent is extended or adjusted under 35 U.S.C. 154(b) by 875 days.

(21) Appl. No.: 10/398,918

(22) PCT Filed: Oct. 15, 2001

(86) PCT No.: PCT/GB01/04589

§ 371 (c)(1),
(2), (4) Date: Jul. 10, 2003

(87) PCT Pub. No.: WO02/33413

PCT Pub. Date: Apr. 25, 2002

(65) Prior Publication Data

US 2004/0014094 A1    Jan. 22, 2004

(51) Int. Cl.
*G01N 33/53* (2006.01)
(52) U.S. Cl. .................. 436/518; 436/514; 436/528; 436/808; 436/810; 436/823; 436/63; 435/287.1; 435/287.2; 435/287.7; 435/287.9; 435/970; 435/7.2; 435/7.92; 422/56; 422/61
(58) Field of Classification Search .............. 435/287.1, 435/287.2, 287.7, 287.9, 970, 975, 515, 518, 435/524, 63, 810, 823; 436/514, 518, 524, 436/63, 810, 823, 528, 808; 422/56, 61
See application file for complete search history.

(56) References Cited

U.S. PATENT DOCUMENTS

| | | | |
|---|---|---|---|
| 4,868,108 A | | 9/1989 | Bahar et al. ..................... 435/7 |
| 4,943,522 A | * | 7/1990 | Eisinger et al. ............ 435/7.25 |
| 5,141,850 A | * | 8/1992 | Cole et al. ................... 436/525 |
| 5,183,742 A | | 2/1993 | Omoto et al. .................. 435/14 |
| 5,451,504 A | * | 9/1995 | Fitzpatrick et al. ........... 435/7.2 |

(Continued)

FOREIGN PATENT DOCUMENTS

GB    2241329    8/1991

(Continued)

*Primary Examiner*—Bao-Thuy L Nguyen
(74) *Attorney, Agent, or Firm*—Perkins Coie LLP

(57) ABSTRACT

The invention provides a dipstick and a kit comprising the dipstick, for testing for the presence of a plurality of different targets in a sample solution which comprises: a dipstick having a plurality of different capture zones and, immobilised to each capture zone, a different capture moiety, each capture moiety capable of capturing a different target; and, separately, a plurality of different detection probes, each detection probe capable of binding to a different target and each detection probe being labelled with or enabling the formation of a detection signal so that the presence of each target is indicated by the formation of a signal at the capture zone for that target; wherein the target for at least two of the capture moieties is a disease causing micro-organism or a marker indicating the existence of a disease, disorder, or condition of the host from which the sample solution was derived, and wherein at least two of the capture moieties are capable of binding to different components or markers of the same disease causing microorganism as targets for those capture moieties. The dipsticks and kits may be used for confirmatory assays of infection by an infectious agent or disease causing microorganisms.

30 Claims, 1 Drawing Sheet

U.S. PATENT DOCUMENTS

| | | | |
|---|---|---|---|
| 5,741,662 A | 4/1998 | Madsen et al. | 435/34 |
| 5,770,460 A | 6/1998 | Pawlak et al. | 436/510 |
| 5,843,691 A | 12/1998 | Douglas et al. | 435/14 |
| 6,454,726 B1 * | 9/2002 | Catt et al. | 600/551 |
| 7,186,508 B2 | 3/2007 | Lee et al. | 435/6 |
| 7,192,701 B2 | 3/2007 | Lee et al. | 435/6 |
| 2004/0048395 A1 | 3/2004 | Lee et al. | |
| 2004/0053256 A1 | 3/2004 | Lee et al. | |
| 2004/0072176 A1 | 4/2004 | Lee et al. | |
| 2007/0190548 A1 | 8/2007 | Lee et al. | |
| 2008/0160516 A1 | 7/2008 | Lee et al. | |
| 2008/0206853 A1 | 8/2008 | Lee et al. | |

FOREIGN PATENT DOCUMENTS

| | | |
|---|---|---|
| WO | 88/08534 | * 11/1988 |
| WO | WO94/23299 | 10/1994 |
| WO | WO94/29696 | 12/1994 |
| WO | WO95/27081 | 10/1995 |
| WO | WO96/19731 | 6/1996 |
| WO | WO97/01758 | 1/1997 |
| WO | WO98/36278 | 8/1998 |

* cited by examiner

Capture Zones

BSA
BSA-FITC
BSA-biotin

Run 1

Conjugates: Navy-anti-FITC

Run 2

Pink-anti-biotin

Run 3

Navy anti-FITC
+
Pink anti-biotin

DIPSTICK ASSAY

This application is a 371 of PCT/GB01/04589 filed on Oct. 15, 2001, the entirety of which is hereby incorporated by reference.

The present invention relates to dipsticks, kits comprising dipsticks, and to dipstick assays for confirming infection by an infectious agent or disease causing microorganism, or for the presence of a disease, disorder or condition not caused by an infectious agent or disease causing microorganism.

After a person has been identified in a general screening procedure as potentially infected with an infectious agent it is often necessary to confirm that this diagnosis is correct. This is particularly the case for diagnosis of HIV, hepatits B virus (HBV), and hepatitis C virus (HCV) infection. An immunoblot assay is typically performed to confirm whether or not the result obtained in the general screening procedure is correct.

However, immunoblot assays have several disadvantages. These assays comprise multiple steps, requiring stepwise addition of different components in a particular order. Incubation and washing steps are necessary after addition of each new component. It may not be possible to complete an assay in less than 5 hours and usually more than 20 hours is required. This is a significant disadvantage because it is desirable to obtain the result as quickly as possible, for example to keep patient waiting times to a minimum. In remote areas, if the general screening and confirmatory assays are not performed during a single visit from a patient, the patient may never obtain the test result because they may be unlikely or unable to return at a later date.

A further disadvantage of immunoblot assays is that specialist equipment is required. Such equipment may not be readily available, particularly in remote areas or resource-poor countries, thus requiring the patient to travel long distances for the tests to be performed. The relatively high cost of immunoblot assays can also reduce their availability in resource-poor countries. Patient and public health can be endangered if tests are not readily available, or if results are not communicated to patients because they are unlikely or unable to return at a later date.

It is desired to provide confirmatory assays which are quick and easy to perform, and which do not require use of specialist equipment.

Figure 1:
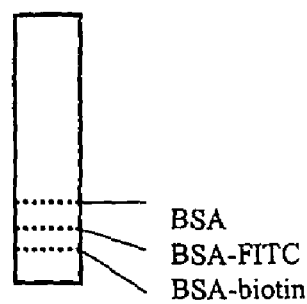
FIG. 1: specific capture of the dye conjugate occurred at each capture zone whether tested singly or in combination.
Figure 1:
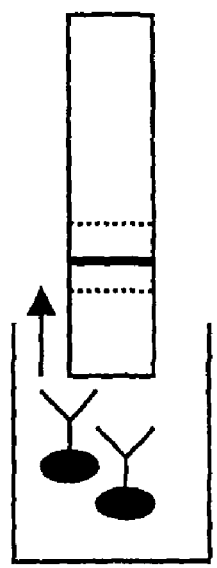
Figure 1:
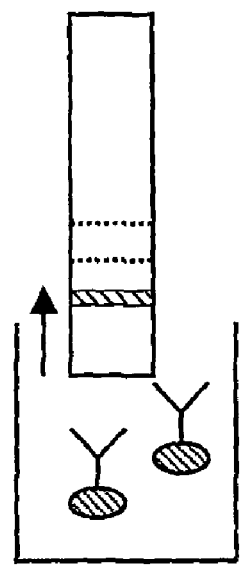
Figure 1:
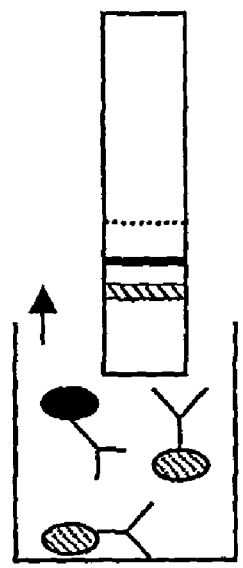

According to a first aspect of the invention there is provided a kit for testing for the presence of a plurality of different targets in a sample solution which comprises:

a dipstick having a plurality of different capture zones and, immobilised to each capture zone, a different capture moiety, each capture moiety capable of capturing a different target; and, separately, a plurality of different detection probes, each detection probe capable of binding to a different target and each detection probe being labelled with or enabling the formation of a detection signal so that the presence of each target is indicated by the formation of a signal at the capture zone for that target; wherein the target for at least two of the capture moieties is an infectious agent or a disease causing micro-organism or a marker indicating the existence of a disease, disorder, or condition of the host from which the sample solution was derived, and wherein at least two of the capture moieties are capable of binding to different components or markers of the same infectious agent or disease causing microorganism, or to different markers for the same disease, disorder, or condition not caused by an infectious agent or disease causing microorganism, as targets for those capture moieties.

The marker may be any marker indicating the existence of any disease, disorder, or condition which it is possible to detect using a dipstick. The marker may, for example, be an antibody raised in the host in response to infection by an infectious agent or disease causing microorganism, or a chemical indicating the existence of a disorder such as a metabolic disorder.

An example of a condition which may be tested for includes HLA subtype. The markers may be markers for pregnancy.

To test for the presence of the plurality of different targets in the sample solution, the plurality of different detection probes may be added to the sample solution and the dipstick immersed in the sample solution so that the capture zones are immersed in the sample solution.

Alternatively, the dipstick may further comprise a contact end, remote from the capture zones, for contacting the sample solution, and be capable of transporting the sample solution by capillary action to the capture zones when the sample solution is contacted with the contact end.

To test for the presence of the plurality of targets in the sample solution, the plurality of detection probes are added to the sample solution to allow binding of the detection probes to target in the sample solution. The contact end of the dipstick is contacted with the sample solution to cause sample solution and target-detection probe complexes to rise up the dipstick by capillary action to the capture zones where they can be detected.

The detection probes may alternatively be releasably immobilised to the dipstick. Thus, according to a second aspect of the invention there is provided a dipstick for testing for the presence of a plurality of different targets in a sample solution which comprises:

a plurality of different capture zones and, immobilised to each capture zone, a different capture moiety, each capture moiety capable of capturing a different target; and a plurality of different detection probes, releasably immobilised to the dipstick, each detection probe capable of binding to a different target and each detection probe being labelled with or enabling the formation of a detection signal so that the presence of each target is indicated by the formation of a signal at the capture zone for that target; wherein the target for at least two of the capture moieties is an infectious agent or a disease causing microorganism or a marker indicating the existence of a disease, disorder, or condition of the host from which the sample solution was derived, and wherein at least two of the capture moieties are capable of binding to different components or markers of the same infectious agent or disease causing micro-organism, or to different markers for the same disease, disorder, or condition not caused by an infectious agent or disease causing microorganism, as targets for those capture moieties.

An advantage of capture moieties being releasably immobilised to the dipstick is that all the components required to obtain a result from a dipstick assay can be present on the dipstick with no other reagents or equipment being required.

To test for the presence of the plurality of different targets in the sample solution using a dipstick of the second aspect of the invention, the dipstick may be immersed in the sample solution so that the detection probes and the capture zones are immersed in the sample solution. Contact of the detection probes with the sample solution causes them to be released from the dipstick so that they can bind to target in the sample solution which can, in turn bind to its capture moiety and thereby allow detection of the target.

Alternatively, a dipstick of the second aspect of the invention may further comprise a contact end, remote from the capture zones, for contacting the sample solution, the detection probes being releasably immobilised between the contact end and the capture zones, wherein the dipstick is capable of transporting the sample solution by capillary action to the capture zones when the sample solution is contacted with the contact end.

To test for the presence of the plurality of targets in the sample solution, the contact end of the dipstick may be contacted with the sample solution to cause the sample solution to rise up the dipstick by capillary action to the capture zones. The detection probes are released by the sample solution as it rises up the dipstick allowing them to bind to target in the sample solution. Detection probe-target complexes can then bind capture moiety at the appropriate capture zone.

The marker may be any marker indicating the existence of any disease, disorder, or condition which it is possible to detect using a dipstick. The marker may, for example, be an antibody raised in the host in response to infection by an infectious agent or disease causing microorganism, or a chemical indicating the existence of a disorder such as a metabolic disorder. An example of a condition which may be tested for includes HLA subtype. The markers may be markers for pregnancy.

Dipsticks and kits of the invention, and tests carried out using these have several advantages. The dipsticks and kits allow reliable diagnosis of infection by an infectious agent or disease causing microorganism. Tests using the dipsticks or kits are simple because they can be performed in a very low number of steps, or even a single step. Minimal training is required, therefore, for a person to be able to perform a test. The tests can be performed rapidly. It is possible to carry out a test in less than one hour, including sample preparation time. No specialist equipment is needed. The kits, dipsticks, and any reagents used can be provided at low cost.

Because of these advantages, it will be appreciated that dipsticks and kits of the invention are particularly advantageous for use in performing confirmatory assays for infection by an infectious agent or disease causing microorganism, or for confirming existence of a disease, disorder, or condition not caused by an infectious agent or disease causing microorganism. Such assays can be performed rapidly, thus keeping patient waiting times to a minimum and allowing screening and confirmatory assays to be performed during a single visit from a patient. Such rapid testing can also make it easier to maintain the confidentiality of the patient. The lack of requirement for specialist equipment and the relatively low cost of performing the assays means that tests can be made readily available. This is a particular advantage in resource-poor countries, and in remote areas where the cost of performing conventional tests, and the requirement for specialist equipment to perform the conventional tests can mean that they are not readily available.

The rapidity with which tests using kits and dipsticks of the invention can be performed means that counseling and treatment can be administered immediately to the patient if a positive result is obtained. This is in contrast to the conventional tests which take much longer to perform. It is often then necessary for a patient to return at a later date which can be several weeks later, and in some cases the patient may never return. Any necessary counseling and treatment would then be significantly delayed or not administered.

Those skilled in the art will appreciate the invention has the advantage that a test or assay can now be designed to take into account any or all known/detectable targets which are available for any specific organism of interest, thereby providing an improved test or assay for that organism.

Detection of different components of the same infectious agent or disease causing microorganism not only allows more reliable diagnosis of an infection, but can also provide information relating to the state of an infection or progression of a disease, disorder or condition.

For example, if a particular antigen is known to occur only during a particular phase of an infection, then knowledge of the presence or absence of this antigen in the patient at the time a sample was taken from the patient could be of assistance in assessing the stage of the infection and, therefore, in determining the most appropriate treatment to be administered.

In some cases, antibodies to both structural and non-structural antigens of an infectious agent or microorganism are seen during an infection and could be used as the basis of an assay of the invention. A serological profile of a patient could be determined which could assist in making decisions regarding further monitoring or treatment of the infection.

It is desirable in any test or assay to reduce or eliminate false negative results, especially when the test or assay is for detecting an infectious agent or a disease causing microorganism or a marker indicating the existence of a disease, disorder or condition caused by an infectious agent or microorganism. According to the invention it has been appreciated that the same species of microorganism may exhibit different potential "targets" due to there being more than one sub-type, strain, variant, mutant etc. of the species. By providing a specific test for multiple targets from the same species the invention can give great specificity to the test yet retain a broad spectrum of applicability, whilst minimising, reducing or eliminating false negative results.

Thus, the invention may also provide a test/assay for distinguishing between or detecting the presence/absence of particular genotypes, serotypes, sub-types, strains, variants, mutants, etc., in a patient sample. This would be of particular value in cases where it is helpful to know whether or not a patient has a particularly virulent or dangerous strain as compared to possibly innocuous or even beneficial/enteric strains.

An example would be to check for *E. coli* 0157 (a very dangerous, often fatal infectious strain) in the presence of other enteric or infective strains. Another example would be in testing patients for influenza infection, where mutation or variation of the strains is known to occur and some forms of influenza are far more pathogenic than others. A further example is detection of different strains of HIV, for example HIV-1 and HIV-2.

In some embodiments of the invention designed to establish whether a patient is infected with a particular genotype, serotype, sub-type, strain, variant, mutant, etc. (referred to collectively as variants below) of infectious agent or disease causing microorganism, different capture moieties each capable of capturing a target specific to each variant may be immobilised to different capture zones. A capture moiety capable of capturing a target common to all of the variants may also be immobilised at a further capture zone. Thus, identification of which variant is present is confirmed in a single test. The identification of a particular variant could allow the most appropriate treatment for the disease caused by that variant to be administered.

Furthermore, according to the invention it has been appreciated that a single sub-type, strain, mutant, variant etc. of a microorganism may exhibit different potential "targets" at different times and/or under different conditions. The present invention provides a kit or dipstick which can be designed to detect such a microorganism regardless of time or condition.

Temporal changes in target may occur for example by virtue of the "life-cycle" of the organism or by virtue of its interaction with a host (i.e. pre- or post-infection).

Conditional changes in targets may occur for example by virtue of external environmental conditions, conditions in an infected host, sample collection, storage, preparation, handling etc.

The infectious agent or microorganism may be a sexually transmitted disease causing infectious agent or microorganism, such as HIV.

The infectious agent or disease causing microorganism may be any other organism such as Hep B virus, Hep C virus, E. coli, H. influenzae, Helicobacter.

A confirmatory assay for HCV may detect any of core, envelope, NS2, NS3, NS4, and NS5 regions, or antibodies reactive with these regions. For example, purified recombinant antigens or proteins or synthetic peptides representing the core, envelope, NS2, NS3, NS4, or NS5 regions could be immobilised as capture moieties.

A confirmatory assay for HIV may detect antibodies to any of the GAG, POL, and ENV regions, for example to p24, p31, gp41, gp120, or gp160. Purified recombinant proteins or synthetic peptides representing these proteins may be immobilised as capture moieties.

Antibodies can be used to capture antigens (HbsAg) in the diagnosis of HBV infection.

It is preferred that different targets are detected in a confirmatory assay to those detected in a screening assay so that the possibility of false diagnosis is further minimised. Different detection formats could additionally or alternatively be used to minimise false diagnosis. In particularly preferred embodiments, it is possible to test for different components or markers for infection by HIV and/or HBV and/or HCV on the same dipstick.

The signal is preferably a visible signal. This has the significant advantage that additional equipment or reagents are not required to visualise and record the results of tests performed using kits and dipsticks of the invention.

The visible signal used for the detection of each target may be the same colour. However, in some circumstances it is possible that use of the same colour in the detection of each target could allow a positive result for a target to be assigned to the wrong target, particularly to a target which binds to an adjacent capture zone where the capture zones are closely spaced on the dipstick. Any confusion is undesirable as it can lead to mistakes in recording which targets are present or absent in the sample solution. In order to avoid making mistakes in recording which targets are present or absent in a sample solution the position on the dipstick at which a positive result has been obtained could be measured. This may be undesirable as it can slow the speed at which the results can be read from the dipstick. Alternatively, a casing indicating the identity of the target for each capture zone could be provided. However, this may be undesirable as the cost and complexity of the test is increased.

It is an advantage of dipsticks and kits of the invention, that the presence of each target can be indicated by a different colour. Hence, the position at which the result is obtained on the dipstick does not need to be taken into account when interpreting the results. Consequently, results can be recorded more rapidly and the risk of incorrectly recording which targets are present or absent in the sample solution is reduced.

Accordingly, the invention provides a kit or dipstick as described above wherein each detection signal is a different colour.

Each detection probe is preferably directly coupled to a visible label. This allows simple and rapid detection of targets without use of other reagents or equipment.

The detection probes may be nucleic acid or non nucleic acid.

At least one of the detection probes may comprise a nucleic acid or nucleic acid analogue capable of hybridising to its target.

The or each detection probe may comprise a "hook" detection probe capable of binding to the target for that detection probe and a "universal" detection probe capable of binding to the hook detection probe. The hook detection probe and the universal detection probe are preferably nucleic acids or nucleic acid analogues.

At least one of the detection probes may comprise an antibody or an antibody fragment.

At least one of the detection probes may comprise a converting enzyme capable of converting a chromogenic substrate thereby enabling formation of the colour indicating the presence of the target for that detection probe.

A kit of the first aspect of the invention may further comprise the or each chromogenic substrate. A dipstick of the second aspect of the invention may be provided as part of a kit with the or each chromogenic substrate.

If one or more chromogenic substrates are required it will be appreciated that the dipstick will normally be immersed in a separate solution comprising the or each chromogenic substrate after the dipstick has been contacted with the sample solution. In some cases in which more than one chromogenic substrate is required, it may be preferred to have a different solution for each chromogenic substrate and to sequentially immerse the dipstick in each different solution after it has been contacted with the sample solution. In other arrangements, a solution comprising the or each chromogenic substrate, or different solutions each comprising a different chromogenic substrate, may be applied directly to the appropriate capture zone(s) of the dipstick.

At least one of the detection probes may comprise a detection ligand which can be bound by a colour labelled detection ligand binding moiety thereby enabling formation of the colour indicating the presence of the target for that detection probe.

A kit of the first aspect of the invention may further comprise one or more colour labelled detection ligand binding moieties. A dipstick of the second aspect of the invention may be provided as part of a kit with one or more colour labelled detection ligand binding moieties.

The dipstick of the kit or the dipstick may comprise a contact end and a conjugate zone between the contact end and the capture zones, the or each colour labelled detection ligand binding moiety being releasably immobilised to the conjugate zone.

The detection ligand may be biotin and a colour labelled detection ligand binding moiety may comprise a biotin binding moiety, such as an anti-biotin antibody, streptavidin, avidin or a derivative thereof which retains biotin binding activity.

The detection ligand may be DNP and a colour labelled detection ligand binding moiety may comprise an anti-DNP antibody.

The detection ligand may be FITC and a colour labelled detection ligand binding moiety may comprise an anti-FITC antibody.

At least one of the detection probes of kits or dipsticks of the invention may comprise nucleic acid which can be bound by a colour labelled nucleic acid thereby enabling formation of a colour indicating the presence of the target for that detection probe.

A kit of the first aspect of the invention may further comprise one or more colour labelled nucleic acid. A dipstick of the second aspect of the invention may be provided as part of a kit with one or more colour labelled nucleic acids.

The capture moieties may be nucleic acid or non nucleic acid.

At least one of the capture moieties may comprise a nucleic acid or nucleic acid analogue.

A capture moiety comprising a nucleic acid or nucleic acid analogue may be capable of binding directly or indirectly to its target. For example, if the target comprises nucleic acid, the nucleic acid or nucleic acid analogue of the capture moiety may be capable of binding to another nucleic acid or nucleic acid analogue bound to the target.

Where the nucleic acid or nucleic acid analogue of the capture moiety is capable of binding to another nucleic acid or nucleic acid analogue bound to the target, it will be appreciated that the latter nucleic acid or nucleic acid analogue should be contacted with, or added to the sample solution in order to detect the presence of the target.

Consequently, a dipstick of the invention may be provided with, or a kit of the invention may include, a nucleic acid or nucleic acid analogue to be contacted with, or added to the sample solution in order for a capture moiety to be able to bind indirectly to its target.

The or each capture moiety may comprise a "hook" capture probe capable of binding to the target for that capture moiety and a "universal" capture probe bound to the hook capture probe. The hook capture probe and the universal capture probe are preferably nucleic acids or nucleic acid analogues.

At least one of the capture moieties may comprise an antibody or antibody fragment.

A capture moiety which comprises an antibody or antibody fragment may be capable of binding directly or indirectly to its target. For example, if the target comprises nucleic acid, the antibody or antibody fragment may be capable of binding to a capture ligand of a capture probe hybridised to the target. The capture probe may comprise a nucleic acid or nucleic acid analogue coupled to a capture ligand.

Where a capture moiety comprises an antibody or antibody fragment capable of binding to a capture ligand of a capture probe, it will be appreciated that the capture probe should be contacted with, or added to the sample solution in order to detect the presence of the target. Consequently, a dipstick of the invention may be provided with, or a kit of the invention may include, a capture probe to be contacted with, or added to the sample solution in order for a capture moiety to be able to bind indirectly to its target.

In some embodiments of the invention, a plurality of different capture probes (which are non nucleic acid or non nucleic acid) may be used to capture a target, each of the different capture probes capable of being bound by a capture moiety. For example, if the target comprises nucleic acid, several different nucleic acid capture probes could be provided, each capable of binding to a different region of the target, but each capture probe comprising a capture ligand which can be bound by the same capture moiety.

Where a target comprises nucleic acid, a capture moiety immobilised at its capture zone may comprise an antibody or antibody fragment bound to the capture ligand of a capture probe capable of hybridising to the nucleic acid of the target.

Examples of suitable capture ligands include biotin, FITC and DNP. These ligands can be bound by anti-biotin, anti-FITC, and anti-DNP antibodies, respectively.

A first capture moiety may be capable of binding to nucleic acid of the infectious agent or disease causing microorganism and a second capture moiety may be capable of binding to an antigen of the same infectious agent or disease causing microorganism.

A first detection probe may be capable of binding to nucleic acid of the infectious agent or disease causing microorganism and a second detection probe may be capable of binding to an antigen of the same infectious agent or disease causing microorganism.

A first detection probe may be capable of binding to a first nucleic acid of the infectious agent or disease causing microorganism and the second detection probe may be capable of binding to a second nucleic acid of the same infectious agent or disease causing microorganism.

A first detection probe may be capable of binding to a first antigen of the infectious agent or disease causing microorganism and a second detection probe may be capable of binding to a second antigen of the same infectious agent or disease causing microorganism.

In some embodiments of the invention, a plurality of different detection probes may be used to detect a target, each of the different detection probes capable of being bound by a colour labelled detection ligand binding moiety. For example, if the target comprises nucleic acid, several different detection probes could be provided, each capable of binding to a different region of the target, but each detection probe comprising a detection ligand which can be bound by the same colour labelled detection ligand binding moiety.

In some embodiments of the invention, there may be the same number of capture moieties as detection probes.

Where different colours are used preferably there are the same number of capture moieties as detection colours.

There is also provided according to the invention use of a kit or a dipstick of the invention for testing for the presence of a plurality of different targets or markers for the same infectious agent or disease causing microorganism, or markers for the same disease, disorder, or condition not caused by an infectious agent or disease causing microorganism in a sample solution.

Examples of suitable colour labels to be used in kits or dipsticks of the invention include a textile dye, a metal sol such as colloidal gold, and/or coloured particles such as coloured latex particles. Textile dyes are particularly preferred because they are stable, inexpensive, and available in a wide range of colours.

Where the detection signal is not provided by a colour label it may be provided by any suitable signal-producing moiety known to those skilled in the art. Examples are (but are not limited to) radio-labels, fluorescence-labels, stains etc.

The sample solution may be a blood sample, a urine sample or it may be derived from a blood sample, urine sample, swab or other sample (for example a tissue sample) obtained from a host in order to test for the presence of a plurality of targets in the host.

In a further aspect of the invention a plurality of different capture moieties capable of binding to different targets which are components or markers of the same infectious agent or disease causing microorganism, or to different markers for the same disease, disorder or condition not caused by an infectious agent or disease causing microorganism, are immobilised to the same capture zone of a dipstick. A plurality of detection probes are provided either separately from the dipstick or releasably immobilised to the dipstick, each detection probe being capable of binding to a different target and each detection probe being labelled with or enabling the formation of a detection signal so that the presence of each target is indicated by the formation of a signal at the capture zone.

EXAMPLE

This example shows that different detection probes labelled with different colours can bind specifically to different capture zones of a dipstick and be clearly distinguished on the dipstick. Although the example does not illustrate detection of the presence of different targets from the same microorganism in a sample solution, a person of ordinary skill in the art will readily appreciate how this may be achieved from its teaching. As noted above, the present invention is not limited solely to the use of coloured signals.

Method:

Dye Washing 0.6 g of navy and pink textile dyes were resuspended in 12 ml of a buffer comprising:

10 mM Sodium Phosphate pH 7.5, 10 mM Sodium Chloride and 1 mM EDTA.**

The dyes were washed by centrifugation followed by resuspension in the above buffer (×3).

Attachment/Conjugation to Antibody
The dyes were diluted to an O.D. reading of:
A=50 at 570 nm for the navy dye
A=25 at 35 nm for the pink dye.
The navy dye was conjugated to an anti-FITC antibody by combining:

500 ul of the navy dye, 3.468 ul of the buffer **, and 25 ug of anti-FITC antibody.

The solution was mixed for 1 hour after which 500 ul of 20% (w/v) blocking agent, such as BSA, was added.

The conjugate was stirred for a further hour after which 500 ul of 50% (w/v) sucrose and Proclin (preservative) was added.

The pink dye was conjugated to an anti-biotin antibody using the method outlined above, the only difference being the initial concentration of the dye (A=25) and the antibody (anti-biotin).

Test System:
BSA, BSA conjugated to FITC and BSA conjugated to biotin were applied to different zones of a nitro-cellulose dipstick at 1.5, 1.3 and 1 cm from the bottom of the dipstick, respectively.

The following reagents were combined for the different test runs:

100 ul of a buffer comprising 50 mM Sodium phosphate pH 7.5, 1% PEG, 1% Triton X-305, 1 mM EDTA, 0.02% Gelatin & 0.02% Ficoll 400 and:

Run1:

50 ul of 10 mM Sodium Phosphate, 10 mM Sodium Chloride, 1 mM EDTA+50 ul of navy dye anti-FITC conjugate Run2:

50 ul of 10 mM Sodium Phosphate, 10 mM Sodium Chloride, 1 mM EDTA+50 ul of pink dye anti-Biotin conjugate Run 3:

50 ul of navy dye anti-FITC conjugate+50 ul of pink dye anti-biotin conjugate.

Results:
As illustrated schematically in FIG. 1, specific capture of the dye conjugates occurred at each capture zone whether tested singly or in combination, i.e. no visual readout at the BSA capture zone 1.5 cm from the base of the membrane and specific signal generation at the BSA-FITC and/or BSA-biotin capture zones. No false positives or change in the colour of the visual readout was observed.

The experiment was repeated using dye conjugates which were dried onto a conjugate pad and released by the migration of sample buffer The same specific result was obtained.

This application claims priority to GB0025245.2, filed Oct. 14, 2000, the entirety of which is hereby incorporated by reference.

The invention claimed is:

1. A kit for testing for the presence of a plurality of different targets in a sample solution which comprises:
a dipstick having a plurality of different capture zones and, immobilized to each capture zone, a different capture moiety, each capture moiety capable of capturing a different target; and
a plurality of different detection probes, each detection probe capable of binding to a different target and each detection probe being labeled with or enabling the formation of a detection signal so that the presence of each target is indicated by the formation of a signal at the capture zone for that target; wherein at least two of the capture moieties bind a component of an infectious agent or a disease causing micro-organism or a marker indicating the existence of a disease, disorder or condition of the host from which the sample solution was derived, and wherein the at least two capture moieties comprise
a first capture moiety that binds a first component or marker of an infectious agent or disease causing micro-organism, and a second capture moiety that binds a second, different, component or marker of the same species of infectious agent or disease causing micro-organism, and wherein the first and second capture moieties have different binding specificities.

2. The kit of claim 1, wherein the dipstick comprises a contact end, remote from the capture zones, for contacting the sample solution, the dipstick being capable of transporting the sample solution by capillary action to the capture zones when the sample solution is contacted with the contact end.

3. A dipstick for testing for the presence of a plurality of different targets in a sample solution which comprises:
a plurality of different capture zones and, immobilized to each capture zone, a different capture moiety, each capture moiety capable of capturing to a different target; and
a plurality of different detection probes, releasably immobilized to the dipstick, each detection probe capable of binding to a different target and each detection probe being labelled with or enabling the formation of a detection signal so that detection of each target is indicated by the formation of a signal at the capture zone for that target; wherein at least two of the capture moieties bind a component of an infectious agent or a disease causing micro-organism or a marker indicating the existence of a disease, disorder or condition of the host from which the sample solution was derived, and wherein the at least two capture moieties comprise
a first capture moiety that binds a first component or marker of an infectious agent or disease causing micro-organism, and a second capture moiety that binds a second, different, component or marker of the same species of infectious agent or disease causing micro-organism, and wherein the first and second capture moieties have different binding specificities.

4. The dipstick according to claim 3 which comprises a contact end, remote from the capture zones, for contacting the sample solution, and in which the detection probes are releasably immobilized between the contact end and the capture zones, wherein the dipstick is capable of transporting the sample solution by capillary action to the capture zones when the sample solution is contacted with the contact end.

5. The kit of claim 1, wherein each detection signal is a different color.

6. The kit of claim 1, wherein at least one of the detection probes comprises a nucleic acid or nucleic acid analogue capable of hybridizing to its target.

7. The kit of claim 1, wherein at least one of the detection probes comprises an antibody or an antibody fragment.

8. The kit of claim 1, wherein at least one of the detection probes is labeled with a textile dye, a metal sol, or colored particles.

9. The kit of claim 1, wherein at least one of the detection probes comprises a converting enzyme capable of converting a chromogenic substrate thereby enabling formation of a color signal indicating the presence of the target for that detection probe.

10. The kit of claim 9 further comprises a separate chromogenic substrate.

11. The kit of claim 1, wherein at least one of the detection probes comprises a detection ligand which can be bound directly by a color labeled detection ligand binding moiety thereby enabling formation of a color indicating the presence of the target for that detection probe.

12. The kit of claim 11 further comprises a color labeled detection ligand binding moiety.

13. The kit of claim 11, wherein the dipstick comprises a contact end and a conjugate zone between the contact end and the capture zones, wherein the color labeled detection ligand binding moiety being releasably immobilized to the conjugate zone.

14. The kit of claim 12, wherein at least one of the detection ligand is biotin and at least one of the color labeled detection ligand binding moieties comprises an anti-biotin antibody.

15. The kit of claim 12, wherein at least one of the detection ligands is FITC or DNP and at least one of the color labeled detection ligand binding moieties comprises an anti-FITC antibody or an anti-DNP antibody, respectively.

16. The dipstick of claim 3, wherein at least one of the detection probes comprises nucleic acid which can be bound by a color labeled nucleic acid thereby enabling formation of the color indicating the presence of the target for that detection probe.

17. The dipstick of claim 16 further comprises a color labeled nucleic acid.

18. The dipstick of claim 3, wherein at least one of the capture moieties comprises a nucleic acid or nucleic acid analogue.

19. The dipstick of claim 3, wherein at least one of the capture moieties comprises an antibody or antibody fragment.

20. The dipstick of claim 3, wherein a first capture moiety is capable of binding to nucleic acid of the disease causing microorganism and a second capture moiety is capable of binding to an antigen of the same disease causing microorganism.

21. The dipstick of claim 3, wherein at least two of the detection probes are capable of binding to different components of the same disease causing micro-organism as targets for those detection probes.

22. The dipstick of claim 21, wherein a first detection probe is capable of binding to nucleic acid of the disease causing microorganism and a second detection probe is capable of binding to an antigen of the same disease causing microorganism.

23. The dipstick of claim 3, wherein the infectious agent or disease causing micro-organism is a sexually transmitted disease causing microorganism.

24. The dipstick of claim 3, wherein the infectious agent or disease causing microorganism is HIV, Hep A virus, Hep B virus, Hep C Virus, *E. coli, H. Influenzae,* or *Helicobacter.*

25. The dipstick of claim 3, wherein the different components or markers are specific for different genotypes, serotypes, sub-types, variants, strains, or mutants of the disease causing microorganism, infectious agent, disorder, or condition.

26. The dipstick of claim 3, wherein the different components or markers are produced and/or are available at different times and/or under different conditions during the course of the disease, disorder, or condition.

27. The dipstick of claim 3, wherein there are the same number of capture moieties as detection signals.

28. A method of using a kit or a dipstick according to claim 1 comprising:
    applying a sample to the dipstick of claim 1,
    detecting any signal formed at the capture zones, and
    relating the detected signals to the presence or absence of the plurality of targets in the sample.

29. The kit of claim 8, wherein the metal sol is colloidal gold.

30. The kit of claim 8, wherein the colored particles are colored latex particles.

* * * * *